`United States Patent` [19]

McNeil et al.

[11] 4,249,020

[45] Feb. 3, 1981

[54] OXYDEHYDROGENATION OF CERTAIN $\geq$ C4 SATURATED OXYHYDROCARBON COMPOUNDS

[75] Inventors: Daniel W. McNeil, New Fairfield; Benjamin Phillips, Riverside, both of Conn.

[73] Assignee: Union Carbide Corporation, New York, N.Y.

[21] Appl. No.: 826,117

[22] Filed: Aug. 19, 1977

[51] Int. Cl.[3] .................... C07C 45/65; C07C 51/377; C07C 67/30
[52] U.S. Cl. .................................. 560/214; 562/599; 252/437; 568/484
[58] Field of Search .................... 560/214; 260/526 N, 260/601 R, 603 R, 603 C; 252/467; 562/599

[56] References Cited

U.S. PATENT DOCUMENTS

| | | | |
|---|---|---|---|
| 3,652,654 | 3/1972 | Tsu | 560/214 |
| 3,770,812 | 11/1973 | Blood et al. | 560/214 |

OTHER PUBLICATIONS

Inoue, Hidetake et al., "Methacrylic acid", Japanese Patent 73 19,614, (See Chemical Abstracts vol. 79. (1973), No. 91,606x).
Otaki, Tadaaki et al., "Methacrolein and Methacrylic Acid from Isobutyraldehyde", Japan, Kokai 73 78,112, (See Chemical Abstracts, vol. 80 (1974), No. 59,466m).
Kita, Teruo et al., "Unsaturated Carboxylic Acids and Esters Thereof by Oxidative Dehydrogenation", Japanese Patent 72 03,088, (See Chemical Abstracts, vol. 76 (1972), No. 154,400).

*Primary Examiner*—Howard T. Mars
*Assistant Examiner*—L. Hendriksen
*Attorney, Agent, or Firm*—Bernard Francis Crowe

[57] ABSTRACT

Certain $C_4$ to $C_9$ saturated acids, esters and aldehydes are oxidatively dehydrogenated catalytically and exothermically to the corresponding $\alpha,\beta$-unsaturated acids, esters and/or aldehydes with certain calcined catalysts containing the elements Mo and V.

16 Claims, No Drawings

OXYDEHYDROGENATION OF CERTAIN ≧C4 SATURATED OXYHYDROCARBON COMPOUNDS

BACKGROUND OF THE INVENTION

1. Field of the Invention

The invention relates to the conversion of certain ≧C4 saturated acids, esters and aldehydes to the corresponding α,β-unsaturated acids, esters and/or aldehydes by a gas phase oxydehydrogenation process.

2. Description of the Prior Art

The catalytic oxydehydrogenation of ≧C4 saturated acids, esters and aldehydes to the corresponding unsaturated acids, esters and/or aldehydes, in the gas phase, is known. The use of the catalysts employed for these reactions to date, however, has certain disadvantages. Halogens, such as iodine and bromine can be used in elemental, organic or inorganic form as catalysts for such reactions (U.S. Pat. Nos. 3,350,169; 3,356,750; 3,442,993; 3,466,149 and 3,770,812 and W. German OLS No. 2,064,576). Although these halogen catalysts provide relatively good results in terms of yields and efficiencies, these good results are seriously offset, from a commercial point of view by the relatively high cost of the catalyst, the difficulty in recovering the catalyst, and the highly corrosive nature of the catalyst.

The use of certain iron based contact catalysts has also been proposed, with and without the use of the halogen catalysts, for these reactions (U.S. Pat. Nos. 3,364,494; 3,855,279 and 3,917,673; U.K. Patent 1,250,749 and W. German OLS No. 2,438,464). In order to obtain relatively good results in terms of yields and efficiencies with these iron containing catalysts it is apparently necessary to conduct the reactions at relatively high temperatures and to use relatively large amounts of gaseous diluent such as nitrogen in the reaction stream.

The oxidation of various ≧C4 unsaturated aldehydes with oxygen to the corresponding unsaturated acid with various heavy metal catalysts is also known. (U.S. Pat. No. 3,833,649; W. German OLS Nos. 2,344,956 and OLS 2,511,076; Japanese Patent application publication Nos. J5-0670-318 and J5-0013-011).

Prior to the present invention, however, it has not been possible to readily oxydehydrogenate saturated ≧C4 acids, esters and aldehydes, in the gas phase at relatively low temperatures with relatively high levels of conversion, yield and efficiency to produce unsaturated compounds having the same numbers of carbon atoms.

The terms percent conversion, percent yield, and percent efficiency which are employed herein with respect to the present invention are defined as follows:

$$\% \text{ conversion} = Sf\text{-}Sr/Sf \times 100 \quad \text{I}$$

$$\% \text{ yield} = P/Sf \times 100 \quad \text{II}$$

$$\% \text{ efficiency} = P/Sf\text{-}Sr \times 100 \quad \text{III}$$

wherein Sf=the moles of starting material fed to the reactor; Sr=moles of starting material recovered in effluent from the reactor; P=moles of product in effluent from the reactor.

SUMMARY OF THE INVENTION

It has been found that certain C4 to C9 saturated acids, esters and aldehydes are oxidatively dehydrogenated catalytically and exothermically to produce the corresponding α,β-unsaturated acids, esters and/or aldehydes at relatively high levels of conversion, selectivity and productivity, with certain calcined catalysts containing the elements Mo, V, and optionally Nb.

An object of the present invention is to provide a process whereby certain C4 to C9 saturated acids, esters and aldehydes are oxidatively dehydrogenated catalytically and exothermically to produce the corresponding α,β-unsaturated acids, esters and/or aldehydes at relatively low temperatures with relatively high levels of conversion, yield and efficiency.

A further object of the present invention is to provide a process whereby isobutyric acid is oxidatively dehydrogenated to methacrylic acid at relatively low temperatures with relatively high levels of conversion, yield and efficiency with certain calcined catalysts containing the elements Mo, V and optionally Nb.

These and other objects of the present invention are achieved by using as a catalyst, in the exothermic oxydehydrogenation of certain C4 to C9 saturated acids, esters and aldehydes, a calcined composition corresponding to the formula:

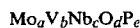

$$Mo_aV_bNb_cO_dP_e$$

a is 16,
b is about 0.5 to 16, and preferably 2 to 8,
c is about 0.0 to 8.0, and preferably 0.0 to 2.0,
d is >0.0,
e is ≧0.0, with the proviso that d+e corresponds to the amounts of O and/or P needed to satisfy the valence requirements of the Mo, V, and Nb in the form of oxides and/or phosphates thereof.

The numerical values of a, b, c, d, and e represent the relative gram-atom ratios of the elements Mo, V, Nb, O, and P, respectively, which are present in the catalyst composition.

The Catalyst

The elements Mo, V and optionally Nb are present in the catalyst composition in combination with oxygen in the form, it is believed of phosphates on various oxides, as such, and possibly as chemical combinations of oxides such as spinels and perovskites.

The catalyst is preferably prepared from a solution or other intimate mixture of soluble compounds (salts, complexes or other compounds) of each of the elements Mo, V and Nb. The solution is preferably an aqueous system. The solution of the element containing compounds is prepared by dissolving sufficient quantities of soluble compounds of each of the elements, so as to provide the desired a:b:c gram-atom ratios of the elements Mo, V and Nb, respectively. To the extent possible the selected compounds of the various elements should be mutually soluble. Where the catalyst is to be used on a support, the compounds of the desired elements are deposited on a particulate porous support usually having the following physical properties, but not limited to these: a surface area of about 0.1 to 500 square meters per gram; an apparent porosity of 30 to 60%; with at least 90% of the pores having a pore diameter in the range of 20-1500 microns; and the form of the particles or pellets being about ⅛ to 5/16 inch in diameter. The deposition is accomplished by immersing the support in the ultimate mixture of all the compounds, evaporating off the major portion of the solvent, and then drying the system at about 80° to 220° C. for 2 to 60 hours. The dried catalyst is then calcined by being heated at about 220° to 550° C. in air or oxygen for ½ to 24 hours to produce the desired $$Mo_aV_bNb_cO_dP_e$$

composition, wherein a, b, c, d and e are as previously defined.

The supports which may be used include silica, aluminum oxide, silicon carbide, zirconia, titania and mixtures thereof.

When used on a support, the supported catalyst usually comprises about 10 to 50 weight % of the catalyst composition, with the remainder being the support.

The molybdenum is preferably introduced into solution in the form of ammonium salts thereof such as ammonium paramolybdate, and organic acid salts of molybdenum such as acetates, oxalates, mandelates and glycolates. Other water soluble molybdenum compounds which may be used are partially water soluble molybdenum oxides, molybdic acid, and the chlorides of molybdenum.

The vanadium is preferably introduced into solution in the form of ammonium salts thereof such as ammonium meta-vanadate and ammonium decavanadate, and organic acid salts of vanadium such as acetates, oxalates and tartrates. Other water soluble vanadium compounds which may be used are partially water soluble vanadium oxides, and the sulfates of vanadium.

When the niobium is used, it is preferably introduced into solution in the form of oxalates. Other sources of this metal in soluble form, which may be used, are compounds in which the metal is coordinated, bonded, or complexed to a beta-diketonate, a carboxylic acid, an amine, an alcohol or an alkanolamine.

When phosphorus is used it is preferably introduced into the catalyst system as phosphoric acid or as a water soluble phosphate.

The catalysts, supported or unsupported, can be used in a fixed or fluidized bed.

The Saturated Organic Compounds

The saturated acids, esters and aldehydes which are oxidatively dehydrogenated in the process of the present invention have the structure $$R_1-\underset{\underset{H}{|}}{\overset{\overset{R_2}{|}}{C}}-\underset{\underset{H}{|}}{\overset{\overset{R_3}{|}}{C}}-\overset{\overset{O}{\|}}{C}-(O-R_4)_m$$
$$(H)_n$$

wherein, $R_1$, $R_2$, and $R_3$ may be H, $CH_3$ or $C_2H_5$, with the proviso that the sum of the carbon atoms in the $R_1$, $R_2$ and $R_3$ radicals is 1 to 3, inclusive, $R_4$ is either H or a primary or secondary alkyl group containing 1 to 4, inclusive, carbon atoms, n is 0 or 1, and m is 1−n.

These saturated organic compounds thus include isobutyric acid. When isobutyric acid is oxidatively dehydrogenated, the corresponding α,β-unsaturated acid would be methacrylic acid.

This reaction is accompanied by the formation of by-products, notably propane, propylene, acrolein, acetone, carbon dioxide, carbon monoxide, and water. These side reactions are favored by high temperatures and can proceed in the absence of catalysts, so it is highly desirable to conduct the oxidative dehydrogenation reaction at as low a temperature as possible. The catalysts of the present invention operate at comparatively lower temperatures than prior art catalysts and have a selective action which makes it possible to reduce greatly the by-product formation. From isobutyric acid, overall efficiencies to methacrylic acid, acetone, and propylene—all useful products—can be 95% or even higher, with over half of the converted starting materials undergoing the desired oxidative dehydrogenation to methacrylic acid. In a commercial process, the propylene could be recycled by treating it with carbon monoxide and water to regenerate isobutyric acid.

The saturated organic compounds may be oxidatively dehydrogenated individually or in combinations thereof.

The Reaction Mixture

The components of the reaction mixture which is used as the feed stream in the process of the present invention and the relative ratios of the components in such mixture are the following:

one mole of saturated organic compound, 0.05 to 6 moles of molecular oxygen (as pure oxygen or in the form of air), 0 to 20 moles of water (in the form of steam).

A feature of the catalysts of the present invention is that they do not require water for good selectivity, in fact, higher efficiencies can usually be obtained without the use of water. Water does not interfere seriously with the catalytic activity, and, of course, some water is always present since it is a co-product of the oxidative dehydrogenation reaction. Operation without added water has the advantage of reducing the heat required for prevaporizing the feed to the reactor, since water has a high heat of vaporization. Also, in the dehydrogenation of esters, reducing the water content of the feed lowers the extent of hydrolysis. The catalysts of the present invention are remarkably stable in their activity, the reaction conditions themselves usually being adequate to maintain clean catalyst surfaces. Thus, whereas many catalytic processes utilize a water feed as a device for maintaining catalytic activity, this is not necessary for the catalysts of this invention.

Other materials which may be used as reaction diluents include oxidatively inert diluents such as nitrogen, carbon dioxide, argon, helium, etc.

The components of the reaction mixture are uniformly admixed prior to being introduced into the reaction zone. The components are preheated, individually or after being admixed, priro to their being introduced into the reaction zone, to a temperature of about 200° to 550° C.

Multi-stage reactors may be employed. For example, it may be preferred to use two reactors in series, with the gaseous effluent from the first being enriched with additional oxygen before being introduced into the second reactor.

Reaction Conditions

The preheated reaction mixture is brought into contact with the catalyst composition, in the reaction zone, under the following conditions:

pressure of about 0.5 to about 20, and preferably, of about 2 to about 10 atmospheres, temperature of about 200° C. to about 550° C., and preferably, of about 275° C. to about 450° C., contact time (reaction mixture in catalyst zone) of about 0.1 to about 20, and preferably of about 0.4 to about 10 seconds, and space velocity of about 50 to about 3000 hours$^{-1}$, preferably of about 100 to 1000 hours$^{-1}$.

The contact time may also be defined as the ratio between the apparent volume of the catalyst bed and the volume of the gaseous reaction mixture fed to the catalyst bed under the given reaction conditions in a unit of time.

The reaction pressure is initially provided by the feed of gaseous reactants and diluents, and after the reaction is commenced, the pressure is maintained, preferably, by the use of suitable back-pressure controllers placed on the gaseous effluent side of the catalyst bed.

The reaction temperature is preferably provided by placing the catalyst bed within a tubular converter whose walls are immersed in a suitable heat transfer medium, such as tetralin or molten salt mixtures which is heated to the desired reaction temperature.

The following examples are merely illustrative of the present invention and are not intended as a limitation on the scope thereof.

The examples provided below disclose the preparation of various catalyst compositions, and the use of such compositions in the oxydehydrogenation of isobutyric acid to methacrylic acid.

The activity of each catalyst was determined in either of the following reactors:

Reactor I

This reaction apparatus consisted essentially of a vertical, electrically-heated quartz tube, twelve inches long and one inch in diameter, packed with a 2-inch layer of quartz glass chips on the bottom, a catalyst bed in the center, and then another layer of quartz glass chips (preheating section) extending from the catalyst bed to the top of the tube. The reactor temperature was controlled by response to a thermocouple located in a quartz glass thermocouple well in the center of the catalyst bed.

In conducting the reaction, a mixture of the saturated aldehyde, acid, or ester; oxygen; and diluent (nitrogen and/or water) was fed through a preheater-vaporizer into the top of the tubular reactor. A small amount of neon (about 1%) was also present to serve as an inert internal standard for gas chromatographic analysis. Samples of the vaporized feed and the effluent from the bottom of the tube were introduced directly, without condensation, into the gas chromatograph for analysis.

Reactor II

This reactor was a laboratory-scale autoclave converter, equipped with an impeller for recirculation of the feed mixture through a central catalyst bed. The reactor is fully described in J. T. Berty, *Chemical Engineering Progress* 70(5) 78–84 (1974) which is incorporated herein by reference.

EXAMPLE I

A molybdenum-vanadium-niobium oxide catalyst was prepared by the following procedure:

67.1 grams of aqueous niobium oxalate solution (14.03% $Nb_2O_3$) was stirred mechanically in an open beaker while 15.9 g of ammonium metavandate was added over a period of ten minutes. Ammonium paramolybdate (100 g) was then added, with continued stirring, giving a dark green mixture. This was poured into shallow quartz dishes and heated in a 220° C. muffle furnace for 16 hours under a slow current of air. The solid product was crushed and screened. The material collected between 5-mesh and 7-mesh (per inch) screens was then heated for 4 hours at 390° C. in an air-purged muffle furnace. The catalyst thus prepared had a calculated elemental ratio of $Mo_{16}V_{3.8}Nb_2$. Its surface area, determined by nitrogen adsorption, was 14.9 square meters per gram.

A 5-ml quantity of the above catalyst was mixed with quartz chips to give a total volume of 20 ml for use as the catalyst bed in Reactor I.

Reactor I was operated, as previously described, using isobutyric acid as the starting material and feeding it at the rate of 5 ml per hour. The reactor temperature, the composition of the feed (mole %), conversion (%), and % efficiency to methacrylic acid, acetone and propylene are set forth in Table I.

EXAMPLE II

Example I was exactly repeated with the exception that the reactor temperature was 350° C. and the composition of the feed was 5.6 mole percent isobutyric acid and 5.2 mole percent oxygen. The results are set forth in Table I.

EXAMPLE III

Example I was exactly repeated with the exception that the reactor temperature was 350° C. and the composition of the feed stream was 3.7 mole percent isobutyric acid and 1.6 mole percent oxygen. The results are set forth in Table I.

EXAMPLE IV

A catalyst was prepared by following the procedure of Method B of British Patent No. 1,250,749, which is incorporated herein by reference. The catalyst had the empirical composition $Bi_2FePb_{0.6}$. A 5-ml sample of 3½- to 5-mesh catalyst was mixed with quartz chips to give a total volume of 20 ml and packed into Reactor I as previously described. Isobutyric acid was fed to the reactor at a rate of 5 ml per hour. The reactor temperature, composition of the feed stream (mole %), conversion (%), and % efficiency to methacrylic acid, acetone and propylene are set forth in Table I.

EXAMPLE V

Reactor I was charged with quartz chips alone. No catalyst was used. Isobutyric acid was fed to the reactor at a rate of 5 ml per hour.

The reactor temperature, composition of the feed stream (mole %), conversion (%), and % efficiency to methacrylic acid, acetone and propylene are set forth in Table I.

EXAMPLE VI

Example V was exactly repeated with the exception that the reactor temperature was 540° C. and the composition of the feed was 4.8 mole percent isobutyric acid and 5.5 mole percent oxygen. The results are set forth in Table I.

EXAMPLE VII

A molybdenum-vanadium-niobium oxide catalyst was prepared by the following procedure: Ammonium metavanadate (40.9 g, 0.350 gram atoms of V) was dissolved in 1.0 liters of water while stirring at 85°–95° C., in a stainless steel, steam-jacketed evaporating dish. To the resulting solution were added 159.2 grams of niobium oxalate solution (14.6% $Nb_2O_5$) (0.175 gram atoms Nb) diluted with 100 ml water and 247 grams of ammonium paramolybdate (1.399 gram atoms Mo) dissolved in 800 ml water. This mixture was heated and dried by evaporating with stirring. Further drying was carried out at a temperature of 120° C. for a period of 16 hours. The dried material was broken to 4×8 mesh and then transferred to a tray fabricated from 10-mesh stainless steel wire screen and calcined in a muffle furnace for 4 hours at 400° in an ambient atmosphere of air. No support was added. The catalyst thus prepared had a calculated elemental ratio of $Mo_{16}V_4Nb_2$.

A 5-ml quantity of the above catalyst was mixed with quartz chips to give a total volume of 20 ml for use as the catalyst bed in Reactor I.

Reactor I was operated, as previously described, using isobutyric acid as the starting material and feeding it at the rate of 5 ml per hour.

The reactor temperature, the composition of the feed (mole %), conversion (%), and % efficiency to methacrylic acid, acetone and propylene are set forth in Table I.

EXAMPLE VIII

Example VII was exactly repeated with the exception that 22.2 mole percent of water was added in the feed stream, replacing an equimolar amount of nitrogen. The results are set forth in Table I.

EXAMPLE IX

The catalyst basket of Reactor II was loaded with 23 g of a $Mo_{16}V_4Nb_2$ catalyst as prepared in Example VII and having a surface area of 7.6 m²/g. The reactor was controlled at 275° C. Isobutyric acid was fed into the reactor at 4.6 ml/hr, the oxygen at 0.24 standard l/min., and the nitrogen at 4.4 standard l/min. The reactor was maintained at 150 psi.

The condensate was analyzed by gas chromatography and found to contain about 80% isobutyric acid and 4% methacrylic acid.

EXAMPLE X

A catalyst was prepared according to the procedure as set forth in Example VII. The catalyst had an elemental ratio of $Mo_{16}V_4Nb_2$. Reactor I was loaded, as previously described, with a 20-ml catalyst bed consisting of 5 ml of neat catalyst mixed with quartz chips. Methyl isobutyrate was fed at a rate of 3.2 ml/hr with the feed consisting of 18% of methyl isobutyrate, 16% of oxygen and 65% of nitrogen. The product stream was passed through a water condenser, and the condensate had the following composition: 24% methyl isobutyrate, 13% methyl methacrylate, 33% isobutyric acid, and 15% methacrylic acid.

TABLE I

| | Catalyst | | | Composition of Feed (mole %) | | | | Efficiency (%) to: | | |
|---|---|---|---|---|---|---|---|---|---|---|
| Ex. | Composition | Surface Area (m²/g) | Reactor Temp. (°C.) | Isobutyric Acid | Oxygen | $H_2O$ | Conversion (%) | Methacrylic Acid | Acetone | Propylene |
| I | $Mo_{16}V_{3.8}Nb_2$ | 14.9 | 275 | 4.9 | 5.9 | — | 15 | 53 | 29 | 11 |
| II | $Mo_{16}V_{3.8}Nb_2$ | 14.9 | 350 | 5.6 | 5.2 | — | 60 | 32 | 25 | 15 |
| III | $Mo_{16}V_{3.8}Nb_2$ | 14.9 | 350 | 3.7 | 1.6 | — | 25 | 44 | 22 | 23 |
| IV | $Bi_2FeP_{0.6}$ | — | 350 | 4.7 | 5.9 | — | 14 | 47 | 23 | 19 |
| V | Quartz | — | 495 | 5.4 | 5.2 | — | 6 | — | 66 | 18 |
| VI | Quartz | — | 540 | 4.8 | 5.5 | — | 17 | 17 | 38 | 18 |
| VII | $Mo_{16}V_4Nb_2$ | 11.1 | 285 | 5.0 | 5.3 | — | 18 | 43 | 32 | 19 |
| VIII | $Mo_{16}V_4Nb_2$ | 11.1 | 285 | 5.4 | 5.6 | 22.2 | 20 | 21 | 43 | 19 |

The results indicate that the catalyst of the present invention (Examples I through III) shows activity and good selectivity at temperatures as low as 275° C. The by-products are predominantly acetone and propylene, both materials of value.

Example IV demonstrates a prior art catalyst. The catalyst of the present invention, of Example I, as compared to the prior art catalyst of Example IV shows the conversion about equal, but the present catalyst performs at a lower temperature and gives methacrylic acid in high efficiency. The present catalyst of Example II is operated at the same temperature as the prior art catalyst of Example IV with higher conversion through lower efficiency.

Comparison of Example III with Example IV demonstrates that at 350° C., flow conditions can be changed to give efficiencies comparable to those of Example IV while still operating at a much higher conversion than Example IV.

Examples V and VI demonstrate an uncatalyzed reaction with no methacrylic acid detectable at reaction temperatures below about 550° C.

Example VII shows a catalyst of the present invention which shows activity and good selectivity at a temperature of about 285° C.

Example VIII demonstrates that the addition of 22.2 mole percent of water to the feed has a deleterious effect on the efficiency, but methacrylic acid is still formed in reasonable yield.

Example IX demonstrates the feasibility of operating the reaction under pressure.

Example X demonstrates that the catalyst of the present invention oxidatively dehydrogenates esters of isobutyric acid.

EXAMPLE XI

A molybdenum-iron-niobium catalyst was prepared, according to the procedure as set forth in Example I, with the exception that 18.5 grams of ferrous acetate (anhydrous) was substituted in place of the ammonium meta vanadate. The catalyst had an elemental ratio of $Mo_{16}Fe_3Nb_2$.

A 5-gram quantity of this catalyst was mixed with enough quartz glass chips to give a total volume of 20 ml for use as the catalyst bed in Reactor I.

Reactor I was operated, as previously described, using isobutyric acid as the starting material and feeding it at the rate of 5 ml per hour.

The reactor temperature, the composition of the feed (mole %), conversion (%) and % efficiency to methacrylic acid, acetone and propylene are set forth in Table II.

EXAMPLE XII

A molybdenum-vanadium-niobium phosphate catalyst was prepared, according to the procedure as set forth in Example I, with the exception that 187 g of dibasic ammonium phosphate was added to the niobium oxalate solution prior to the addition of the ammonium meta vanadate. The catalyst had an elemental ratio of $Mo_{16}V_4Nb_2P_4$.

A 5-gram quantity of this catalyst was mixed with enough quartz glass chips to give a total volume of 20 ml for use as the catalyst bed in Reactor I.

Reactor I was operated, using isobutyric acid as the starting material, as in Example XI.

The results are set forth in Table II.

EXAMPLE XIII

Example XII was exactly repeated with the exception that the reactor temperature was 350° C.

The results are set forth in Table II.

EXAMPLE XIV

A molybdenum-vanadium catalyst was prepared, according to the procedure as set forth in Example I, with the exception that 57.6 g of distilled water was substituted for the niobium oxalate solution. The catalyst had an elemental ratio of $Mo_{16}V_4$.

Reactor I was packed and operated, using isobutyric acid as the starting material, as in Example XI.

The results are set forth in Table II.

EXAMPLE XV

A 5-gram quantity of the $Mo_{16}V_4Nb_2$ catalyst used in Examples 1 through 3 was mixed with quartz chips to give a total volume of 20 ml for use as the catalyst bed in Reactor I.

Isobutyraldehyde was fed into the reactor at a rate of 9 ml/hr. The oxygen and nitrogen flows were adjusted so that the total feed contained 5.0% oxygen and 5.5% isobutyraldehyde. At 350° C. reactor temperature, the calculated efficiency to methacrolein was 36% and to isobutyric acid was 3%. The conversion was 53%.

EXAMPLE XVI

The oxidative dehydrogenation of propionic acid was studied in Reactor I, which was charged with a catalyst bed consisting of 5 grams of the $Mo_{16}V_{3.8}Nb_2$ oxide catalyst of Example I, diluted with quartz glass chips to a total volume of 20 ml.

In conducting the reaction, propionic acid was metered by means of a syringe pump at the rate 7.35 ml/hr. into a prevaporizer where it was diluted with nitrogen, oxygen and neon to give a vaporized feed containing 5% propionic acid, 5% oxygen, 89% nitrogen and 1% neon by volume. This was passed through the reactor at several temperatures in the range of 250° C. to 350° C. The effluent from the reactor was condensed and analyzed by gas chromatography using a "Poropak-T" column at 200° C. and a flame ionization detector. The principal product of the reaction was acetic acid rather than acrylic acid. No acrylic acid was obtained at 250° C. At higher temperatures small amounts of acrylic acid were formed, but at 350° C. the condensate analyzed as follows: acetic acid 20 GC/area percent; propionic acid 75 GC/area percent; acrylic acid 5 GC/area percent.

It was concluded that the catalyst was not adequately selective for use in manufacturing acrylic acid from propionic acid.

TABLE II

| | Catalyst | | Reactor Temp. (°C.) | Composition of Feed (mole %) | | Conversion (%) | Efficiency (%) to: | | |
|---|---|---|---|---|---|---|---|---|---|
| Ex. | Composition | Surface Area (m²/g) | | Isobutyric Acid | Oxygen | | Methacrylic Acid | Acetone | Propylene |
| XI | $Mo_{16}Fe_3Nb_2$ | 7.5 | 300 | 4.5 | 4.9 | 18 | 35 | 43 | 14 |
| XII | $Mo_{16}V_4Nb_2P_4$ | 4.5 | 300 | 5.2 | 4.9 | 12 | 59 | 21 | 14 |
| XIII | $Mo_{16}V_4Nb_2P_4$ | 4.5 | 350 | 5.2 | 4.9 | 32 | 53 | 23 | 20 |
| XIV | $Mo_{16}V_4$ | — | 350 | 5.3 | 4.9 | 34 | 40 | 20 | 35 |

The results indicate that a catalyst containing Mo and Nb and using iron in place of vanadium (Example XI) gives inferior results in conversion and efficiency.

Examples XII and XIII demonstrate that the phosphate catalysts of the present invention give high efficiencies to methacrylic acid.

Example XIV demonstrates the conversion of isobutyric acid to methacrylic acid using a $Mo_{16}V_4$ catalyst, of the present invention.

Example XV demonstrates the conversion of isobutyraldehyde to methacrolein with a catalyst of the present invention.

Obviously, other modifications and variations of the present invention are possible in light of the above teachings. It is, therefore, to be understood that changes may be made in the particular embodiments of this invention described which are within the full intended scope of the invention as defined by the appended claims.

What is claimed is:

1. A process for converting at least one saturated organic compound having the structure $$R_1-\underset{\underset{H}{|}}{\overset{\overset{R_2}{|}}{C}}-\underset{\underset{H}{|}}{\overset{\overset{R_3}{|}}{C}}-\underset{\underset{(H)_n}{|}}{\overset{\overset{O}{\|}}{C}}-(O-R_4)_m$$

wherein $R_1$, $R_2$ and $R_3$ may each be H, $CH_3$ or $C_2H_5$, with the proviso that the sum of the carbon atoms in the $R_1$, $R_2$ and $R_3$ radicals is 1 to 3, inclusive, $R_4$ is either H or $CH_3$, n is 0 or 1, and m is 1−n, to the corresponding α,β-unsaturated acid, ester and/or aldehyde which comprises catalytically oxidatively dehydrogenating the saturated organic compound exothermically by contacting said saturated organic compound with a calcined catalyst composition having the formula $$Mo_aV_bNb_cO_dP_e$$

a is 16,
b is about 0.5 to 16,
where c is up to 8 but greater than 0,
d is >0.0,
e is ≧0.0,
with the proviso that d+e corresponds to the amounts of O and/or P needed to satisfy the valence requirements of the Mo, V, and Nb in the form of oxides and/or phosphates thereof.

2. A process as in claim 1 in which b is 2.0 to 8.

3. A process as in claim 1 in which c is up to 2 but greater than 0.

4. A process as in claim 1 in which c is 2.0.

5. A process as in claim 1 in which e is 0.

6. A process as in claim 1 in which n is 0.

7. A process as in claim 6 in which $R_4$ is H.

8. A process as in claim 7 in which said saturated compound comprises isobutyric acid.

9. A process as in claim 1 in which m is 0.

10. A process as in claim 9 in which said saturated compound comprises isobutyraldehyde.

11. A process as in claim 1 in which $R_4$ is $CH_3$.

12. A process as in claim 11 in which said saturated compound comprises methyl isobutyrate.

13. A process as in claim 1 which is conducted at a temperature of about 200° to 550° C.

14. A process as in claim 13 which is conducted at a pressure of about 0.5 to 20 atmospheres.

15. A process as in claim 1 in which said catalyst is supported on an inert support.

16. A process as in claim 1 which is conducted in the gas phase.

* * * * *